(12) United States Patent
Huff et al.

(10) Patent No.: US 12,208,023 B2
(45) Date of Patent: Jan. 28, 2025

(54) ORTHOPAEDIC SURGICAL INSTRUMENT SYSTEMS AND ASSOCIATED METHODS OF USE

(71) Applicant: DePuy Ireland Unlimited Company, Ringaskiddy (IE)

(72) Inventors: Daniel N. Huff, Warsaw, IN (US); Kaela A. Wong, Wayne, NJ (US); Niki Gosling, Leeds (GB); Ivan Velikanov, Pudsey (GB); Talha Mansur, Huddersfield (GB); Paige Buckley, South Harrow (GB); Joanne Lewis, Leeds (GB)

(73) Assignee: DEPUY IRELAND UNLIMITED COMPANY, Ringaskiddy (IE)

(*) Notice: Subject to any disclaimer, the term of this patent is extended or adjusted under 35 U.S.C. 154(b) by 53 days.

(21) Appl. No.: 17/081,447

(22) Filed: Oct. 27, 2020

(65) Prior Publication Data

US 2022/0125603 A1 Apr. 28, 2022

(51) Int. Cl.
*A61F 2/38* (2006.01)
*A61F 2/00* (2006.01)
*A61F 2/46* (2006.01)
*A61B 17/17* (2006.01)
*A61F 2/30* (2006.01)

(52) U.S. Cl.
CPC .......... *A61F 2/4684* (2013.01); *A61F 2/0095* (2013.01); *A61F 2/3859* (2013.01); *A61F 2/3868* (2013.01); *A61F 2/461* (2013.01); *A61B 17/1764* (2013.01); *A61F 2002/30616* (2013.01); *A61F 2/389* (2013.01)

(58) Field of Classification Search
CPC .... A61F 2/4684; A61F 2/0095; A61F 2/3859; A61F 2/3868; A61F 2/461; A61F 2002/30616; A61B 17/1764
See application file for complete search history.

(56) References Cited

U.S. PATENT DOCUMENTS

| | | | |
|---|---|---|---|
| 5,318,543 | A | 6/1994 | Ross et al. |
| 5,480,440 | A | 1/1996 | Kambin |
| 5,597,384 | A | 1/1997 | Walker et al. |
| 5,776,201 | A | 7/1998 | Colleran et al. |
| 5,779,053 | A | 7/1998 | Partika et al. |
| 6,158,437 | A | 12/2000 | Vagley |

(Continued)

FOREIGN PATENT DOCUMENTS

| | | |
|---|---|---|
| CN | 103068328 B | 3/2017 |
| CN | 104013456 B | 1/2018 |

(Continued)

OTHER PUBLICATIONS

Extended European Search Report for Application No. EP 18 19 4429 dated Feb. 4, 2019, 9 pages.

(Continued)

*Primary Examiner* — Megan Y Wolf
(74) *Attorney, Agent, or Firm* — Barnes & Thornburg LLP

(57) ABSTRACT

A surgical instrument system includes a commonly-sized orthopaedic surgical instrument assembly for use in implanting a femoral component, along with a number of orthopaedic surgical instrument assemblies having varying sizes of instruments of use in implanting a tibial tray component and a patella component.

17 Claims, 3 Drawing Sheets

(56) References Cited

U.S. PATENT DOCUMENTS

| | | | |
|---|---|---|---|
| 6,783,004 B1 | 8/2004 | Rinner | |
| 6,793,078 B2 | 9/2004 | Roshdy | |
| 6,855,150 B1 * | 2/2005 | Linehan | A61F 2/461 623/20.18 |
| 8,701,890 B2 | 4/2014 | Bertazzoni et al. | |
| 10,390,867 B2 | 8/2019 | Sixto et al. | |
| 2003/0121821 A1 | 7/2003 | Roshdy | |
| 2005/0033430 A1 | 2/2005 | Powers et al. | |
| 2006/0124486 A1 | 6/2006 | Faust et al. | |
| 2006/0217815 A1 | 9/2006 | Gibbs et al. | |
| 2006/0223035 A1 | 10/2006 | Fischer | |
| 2007/0034538 A1 | 2/2007 | Landis | |
| 2008/0021567 A1 | 1/2008 | Meulink et al. | |
| 2009/0194446 A1 | 8/2009 | Miller et al. | |
| 2010/0065456 A1 | 3/2010 | Junk et al. | |
| 2011/0071572 A1 | 3/2011 | Sixto et al. | |
| 2011/0186456 A1 * | 8/2011 | Bertazzoni | A61F 2/38 606/89 |
| 2012/0041445 A1 | 2/2012 | Roose et al. | |
| 2013/0006371 A1 * | 1/2013 | Wogoman | A61F 2/461 623/20.21 |
| 2014/0224704 A1 | 8/2014 | Bertazzoni et al. | |
| 2014/0243834 A1 | 8/2014 | Chaney et al. | |
| 2016/0367370 A1 * | 12/2016 | Kim | A61B 50/20 |
| 2017/0333212 A1 | 11/2017 | Wolfson et al. | |
| 2019/0083284 A1 | 3/2019 | Stoller et al. | |

FOREIGN PATENT DOCUMENTS

| | | |
|---|---|---|
| DE | 202007000934 U1 | 4/2007 |
| EP | 1393695 A1 | 3/2004 |
| FR | 2904527 A1 | 2/2008 |
| JP | H07178116 A | 7/1995 |
| JP | 2013505071 A | 2/2013 |
| RU | 2360637 C1 | 7/2009 |
| WO | 0152762 A1 | 7/2001 |
| WO | 2004006811 A2 | 1/2004 |
| WO | 2005016183 A1 | 2/2005 |

OTHER PUBLICATIONS

Zimmer, Inc., "Instrument Care, Cleaning and Sterilization Instruction"; www.zimmer.com; Feb. 6, 2004; Retrieved Jan. 6, 2011 from the Internet URL: http://www.zimmer.co.nz/web/enUS/pdf/Surgical.sub.-Cleaning.sub.-I-Instructions.sub.-Final.pdf; Copyrgt. 1987, 1988, 2002 Zimmer Inc.; USA.

International Search Report for Application No. PCT/EP 2021/079828 dated Jan. 27, 2022, 6 pages.

Arthrex et al.. "iBalance (TM) TKA AR-613-S", Jan. 28, 2020 (Jan. 28, 2020).

"Expert Precision Systems Revision Knee: Redefined", Oct. 1, 2016 (Oct. 1, 2016).

* cited by examiner

ORTHOPAEDIC SURGICAL INSTRUMENT SYSTEMS AND ASSOCIATED METHODS OF USE

TECHNICAL FIELD

The present disclosure relates generally to orthopaedic instruments for use in the performance of an orthopaedic joint replacement procedure, and more particularly to orthopaedic surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

During either a primary or revision knee surgery, the orthopaedic surgeon typically uses a variety of different orthopaedic surgical instruments such as, for example, cutting blocks, reamers, drill guides, prosthetic trials, and other surgical instruments to prepare the patient's bones to receive the knee prosthesis. Such surgical instruments may be constructed of either metal or polymer materials and are generally designed to be reusable. After use, reusable surgical instruments are kitted into trays, sterilized, and returned to the operating room for use in a subsequent procedure.

SUMMARY

According to one aspect of the disclosure, a surgical instrument system includes a plurality of orthopaedic surgical instruments including (i) a plurality of femoral trial components, with each of the plurality of femoral trial components having a common size. The orthopaedic surgical instruments also include a plurality of tibial bearing trial components, with each of the plurality of tibial bearing trial components having a common size that is the same as the common size of the plurality of femoral trial components. Each of the plurality of tibial bearing trial components includes a locking mechanism. The orthopaedic surgical instruments also include a plurality of tibial tray trial components, with each of the tibial tray trial components having a size that is different from the size of at least some of the other of the plurality of tibial tray trial components. Each of the plurality of tibial tray trial components includes a locking mechanism that mates with the locking mechanisms of the plurality of tibial bearing trial components such that each of the plurality of tibial bearing trial components is configured to be separately coupled to each of the plurality of tibial tray trial components. The surgical instrument system also includes a first instrument sterilization tray having a plurality of instrument retainers configured to retain the orthopaedic surgical instruments during sterilization and transport thereof. The first instrument sterilization tray is devoid of any of the plurality of tibial tray trial components when any of the plurality of instrument retainers of the first instrument sterilization tray have one of the plurality of femoral trial components or one of the plurality of tibial bearing trial components retained thereto. The surgical instrument system further includes a second instrument sterilization tray having a plurality of instrument retainers configured to retain the orthopaedic surgical instruments during sterilization and transport thereof. The second instrument sterilization tray is devoid of any of the plurality of femoral trial components and any of the plurality of tibial bearing trial components when any of the plurality of instrument retainers of the second instrument sterilization tray have one of the plurality of tibial tray trial components retained thereto.

The plurality of femoral trial components may include a right femoral trial component and a left femoral trial component.

The plurality of tibial bearing trial components may include a rotating-platform tibial bearing trial component.

The plurality of tibial bearing trial components may include a fixed-bearing tibial bearing trial component.

The surgical instrument assembly may also include a femoral cutting block having a size that is the same as the common size of the plurality of femoral trial components.

The surgical instrument assembly may also include a femoral notch guide having a size that is the same as the common size of the plurality of femoral trial components.

The surgical instrument assembly may also include a femoral finishing guide having a size that is the same as the common size of the plurality of femoral trial components.

Each of the plurality of tibial tray trial components may include a tibial plate trial component and a removable tibial post trial component.

The plurality of orthopaedic surgical instruments may also include a plurality of patella trial components, with each of the patella trial components having a size that is different from the size of at least some of the other of the plurality of patella trial components. At least one of the plurality of patella trial components includes a bearing surface configured to articulate with each of the plurality of femoral trial components. A third instrument sterilization tray has a plurality of instrument retainers configured to retain the orthopaedic surgical instruments during sterilization and transport thereof. The third instrument sterilization tray is devoid of any of the plurality of femoral trial components and any of the plurality of tibial bearing trial components when any of the plurality of instrument retainers of the third instrument sterilization tray have one of the plurality of patella trial components retained thereto.

According to another aspect, a surgical instrument system includes a plurality of orthopaedic surgical instruments having a right femoral trial component and a left femoral component. The right and left femoral trial components are the same size. The orthopaedic surgical instruments also include tibial bearing trial components, with the tibial bearing components being the same size as the right and left femoral trial components. The tibial bearing components include a locking mechanism. The plurality of orthopaedic surgical instruments also includes a plurality of tibial tray trial components, with each of the tibial tray trial components having a size that is different from the size of at least some of the other of the plurality of tibial tray trial components. Each of the plurality of tibial tray trial components includes a locking mechanism that mates with the locking mechanisms of the tibial bearing components such that the tibial bearing components are configured to be separately coupled to each of the plurality of tibial tray trial components. The system also includes a first instrument sterilization tray having a plurality of instrument retainers configured to retain the orthopaedic surgical instruments during sterilization and transport thereof. The first instrument sterilization tray is devoid of any of the plurality of tibial tray trial components when the plurality of instrument retainers of the first instrument sterilization tray has (i) at least one of the right and left femoral trial components, and (ii) at least one of the tibial bearing trial components retained thereto. The system also includes a second instrument sterilization tray having a plurality of instrument retainers configured to retain the orthopaedic surgical instruments during sterilization and transport thereof. The second instrument sterilization tray is devoid of both the right and left femoral trial components and the tibial bearing trial components when any of the plurality of instrument retainers of the second instrument sterilization tray has at least one of the plurality of tibial tray trial components retained thereto.

The tibial bearing trial components may be embodied as rotating-platform tibial bearing trial components or fixed-bearing tibial bearing trial components.

The surgical instrument assembly may also include a femoral cutting block that is the same size as the right and left femoral trial components.

The surgical instrument assembly may also include a femoral notch guide that is the same size as the right and left femoral trial components.

The surgical instrument assembly may also include a femoral finishing guide that is the same size as the right and left femoral trial components.

Each of the plurality of tibial tray trial components may include a tibial plate trial component and a removable tibial post trial component.

The plurality of orthopaedic surgical instruments may also include a plurality of patella trial components, with each of the patella trial components having a size that is different from the size of at least some of the other of the plurality of patella trial components. At least one of the plurality of patella trial components includes a bearing surface configured to articulate with both the right and left femoral trial components. A third instrument sterilization tray has a plurality of instrument retainers configured to retain the orthopaedic surgical instruments during sterilization and transport thereof. The third instrument sterilization tray is devoid of both the right and left femoral trial components and the tibial bearing trial components when any of the plurality of instrument retainers of the third instrument sterilization tray have at least one of the plurality of patella trial components retained thereto.

According to another aspect, a method of using a surgical instrument system includes positioning a plurality of commonly-sized femoral trial components and tibial bearing trial components in a first instrument sterilization tray and a plurality of differently-sized tibial tray trial components in a second instrument sterilization tray such that (i) the first instrument sterilization tray is devoid of any of the plurality of differently-sized tibial tray trial components, and (ii) the second instrument sterilization tray is devoid of any of the plurality of commonly-sized femoral trial components and tibial bearing trial components. The method also includes sterilizing the first instrument tray and the second instrument tray. The method further includes assembling one of the tibial bearing trial components from the first instrument sterilization tray to one of the tibial tray trial components from the second instrument sterilization tray and thereafter utilizing the assembled components during performance of an orthopaedic surgical procedure.

The method may also include positioning a femoral cutting block that is the same size as the plurality of commonly-sized femoral trial components and tibial bearing trial components in the first instrument sterilization tray.

The method may also include positioning a femoral notch guide that is the same size as the plurality of commonly-sized femoral trial components and tibial bearing trial components in the first instrument sterilization tray.

The method may also include positioning a femoral finishing guide that is the same size as the plurality of commonly-sized femoral trial components and tibial bearing trial components in the first instrument sterilization tray.

The method may also include positioning a plurality of differently-sized patella trial components in a third instrument sterilization tray such that the third instrument sterilization tray is devoid of any of the plurality of commonly-sized femoral trial components and tibial bearing trial components.

According to another aspect, a method of using a surgical instrument system includes positioning a plurality of commonly-sized femoral trial components and tibial bearing trial components in a first instrument sterilization tray and a plurality of differently-sized tibial tray trial components in each of a second instrument sterilization tray and a third instrument sterilization tray such that (i) the first instrument sterilization tray is devoid of any of the plurality of differently-sized tibial tray trial components, and (ii) both the second instrument sterilization tray and the third instrument sterilization tray are devoid of any of the plurality of commonly-sized femoral trial components and tibial bearing trial components. The method also includes positioning a number of non-size-specific instruments configured for use in a cemented installation procedure of the plurality of tibial tray trial components in the second instrument sterilization tray. The method also includes positioning a number of non-size-specific instruments configured for use in a cementless installation procedure of the plurality of tibial tray trial components in the third instrument sterilization tray. The method also includes sterilizing the first instrument sterilization tray, the second instrument sterilization tray, and the third instrument sterilization tray. The method further includes selecting one of the second instrument sterilization tray or the third instrument sterilization tray. The method yet further includes assembling one of the tibial bearing trial components from the first instrument sterilization tray to one of the tibial tray trial components from the selected second instrument sterilization tray or third instrument sterilization tray and thereafter utilizing the assembled components during performance of an orthopaedic surgical procedure.

A number of non-size-specific instruments configured for use in a cemented manual installation procedure of the plurality of tibial tray trial components may be positioned in the second instrument sterilization tray, with a number of non-size-specific instruments configured for use in a cementless manual installation procedure of the plurality of tibial tray trial components being positioned in the second instrument sterilization tray.

A number of non-size-specific instruments configured for use in a cemented robotic installation procedure of the plurality of tibial tray trial components may be positioned in the second instrument sterilization tray, with a number of non-size-specific instruments configured for use in a cementless robotic installation procedure of the plurality of tibial tray trial components being positioned in the second instrument sterilization tray.

The method may also include positioning a plurality of differently-sized patella trial components in a fourth instrument sterilization tray and a fifth instrument sterilization tray such that both the fourth instrument sterilization tray and the fifth instrument sterilization tray are devoid of any of the plurality of commonly-sized femoral trial components and tibial bearing trial components. The method may further include positioning a number of non-size-specific instruments configured for use in a cemented installation procedure of the plurality of patella trial components in the fourth instrument sterilization tray, and positioning a number of non-size-specific instruments configured for use in a cementless installation procedure of the plurality of patella trial components in the fifth instrument sterilization tray. The method may include sterilizing the fourth instrument sterilization tray and the fifth instrument sterilization tray. The method may also include selecting one of the fourth instrument sterilization tray or the fifth instrument sterilization tray, and trialing one of the femoral trial components from the first instrument sterilization tray with one of the patella trial components from the selected fourth instrument sterilization tray or fifth instrument sterilization tray and during performance of the orthopaedic surgical procedure.

A number of non-size-specific instruments configured for use in a cemented manual installation procedure of the plurality of patella trial components may be positioned in the fourth instrument sterilization tray, with a number of non-size-specific instruments configured for use in a cementless manual installation procedure of the plurality of patella trial components being positioned in the fifth instrument sterilization tray.

A number of non-size-specific instruments configured for use in a cemented robotic installation procedure of the plurality of patella trial components may be positioned in the fourth instrument sterilization tray, with a number of non-size-specific instruments configured for use in a cementless robotic installation procedure of the plurality of patella trial components being positioned in the fifth instrument sterilization tray.

BRIEF DESCRIPTION OF THE DRAWINGS

The detailed description particularly refers to the following figures, in which.

DETAILED DESCRIPTION OF THE DRAWINGS

Figure 1:
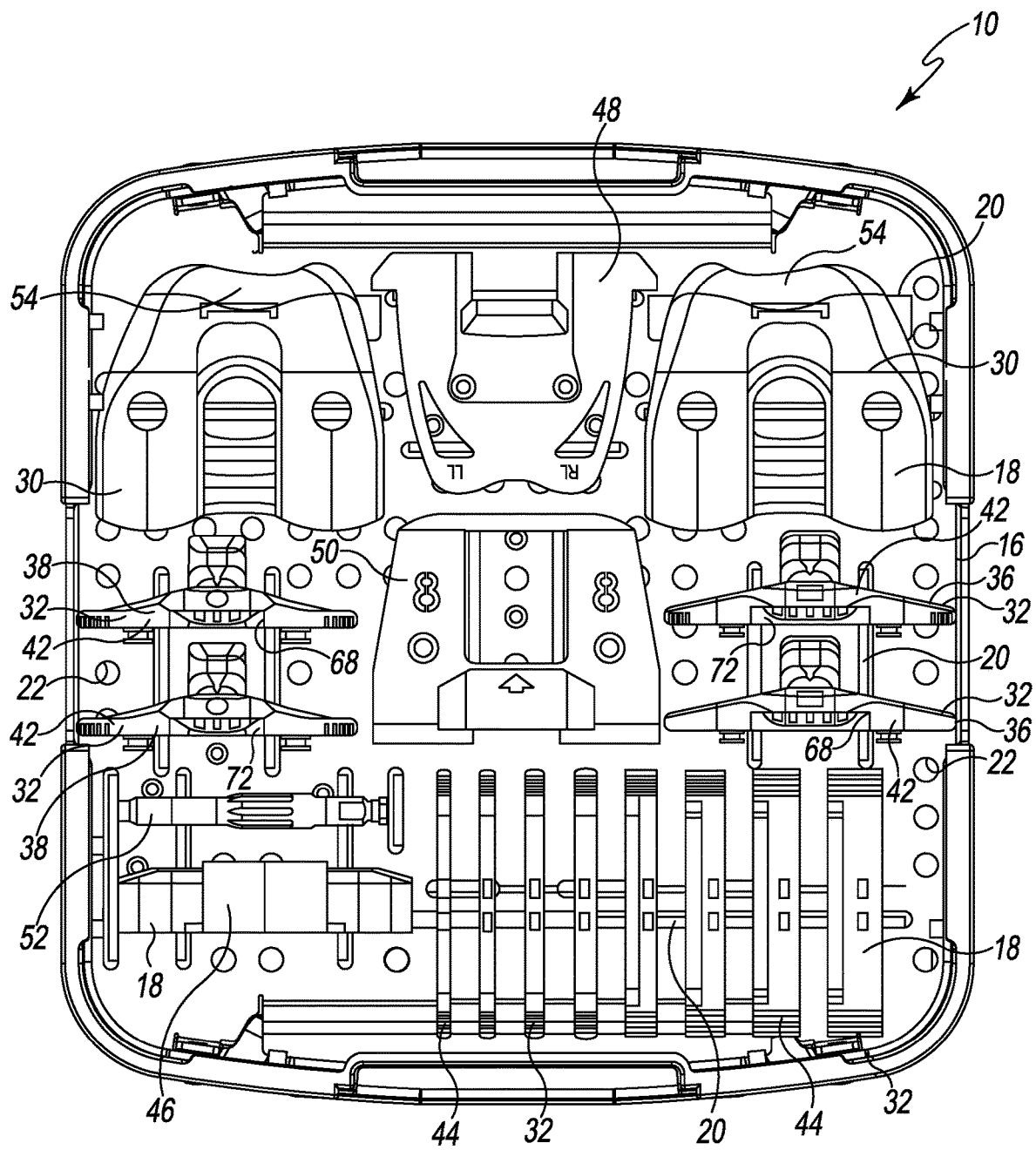
FIG. 1 is an elevation view of an exemplary embodiment of an orthopaedic surgical instrument assembly that includes femoral trial components and tibial bearing trial components, all of which are of a common size.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
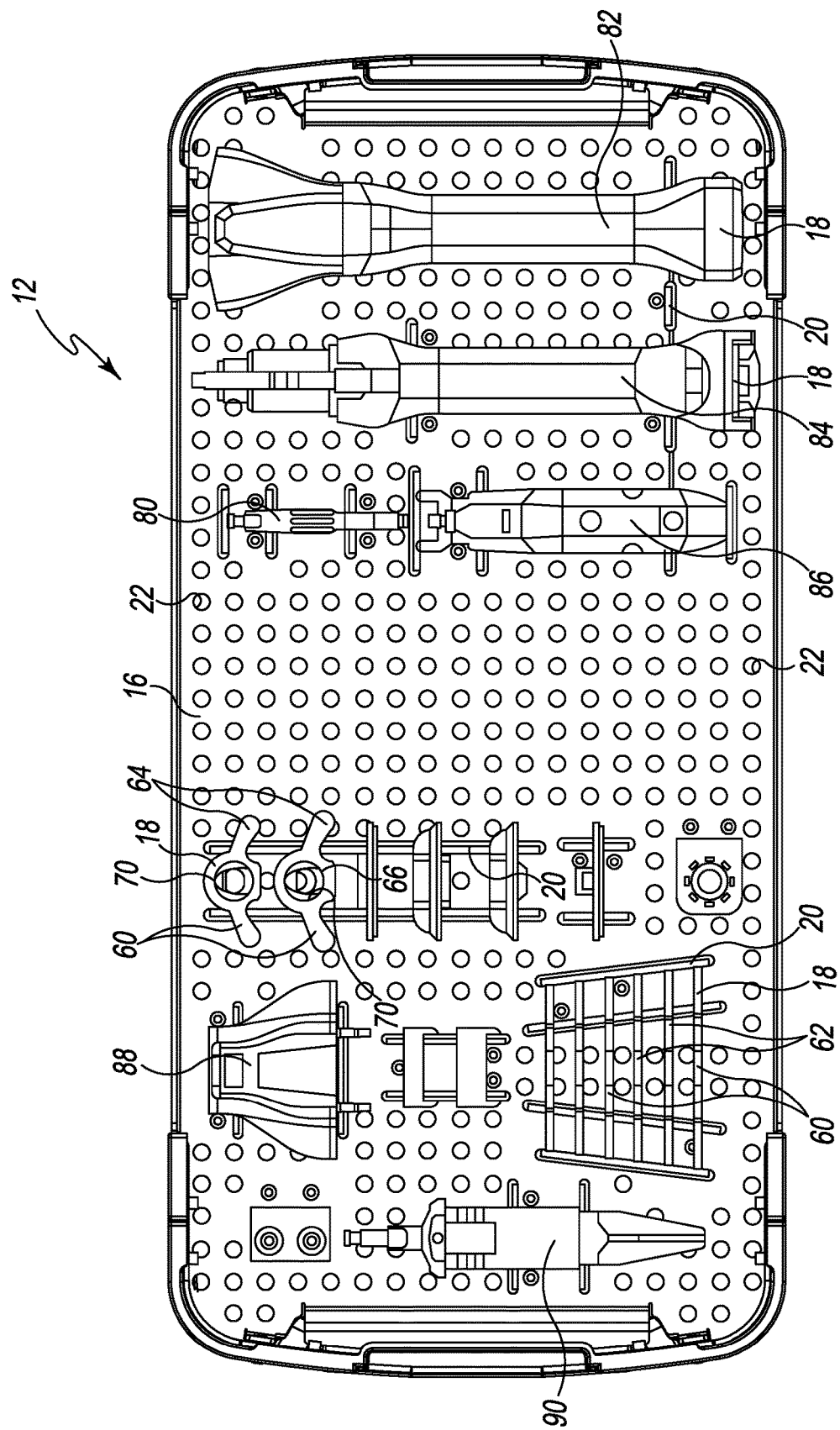
FIG. 2 is an elevation view of an exemplary embodiment of an orthopaedic surgical instrument assembly that includes tibial tray trial components of varying sizes, each of which is configured to be separately coupled to the tibial bearing trial components of the assembly of FIG. 1.
Figure 3:
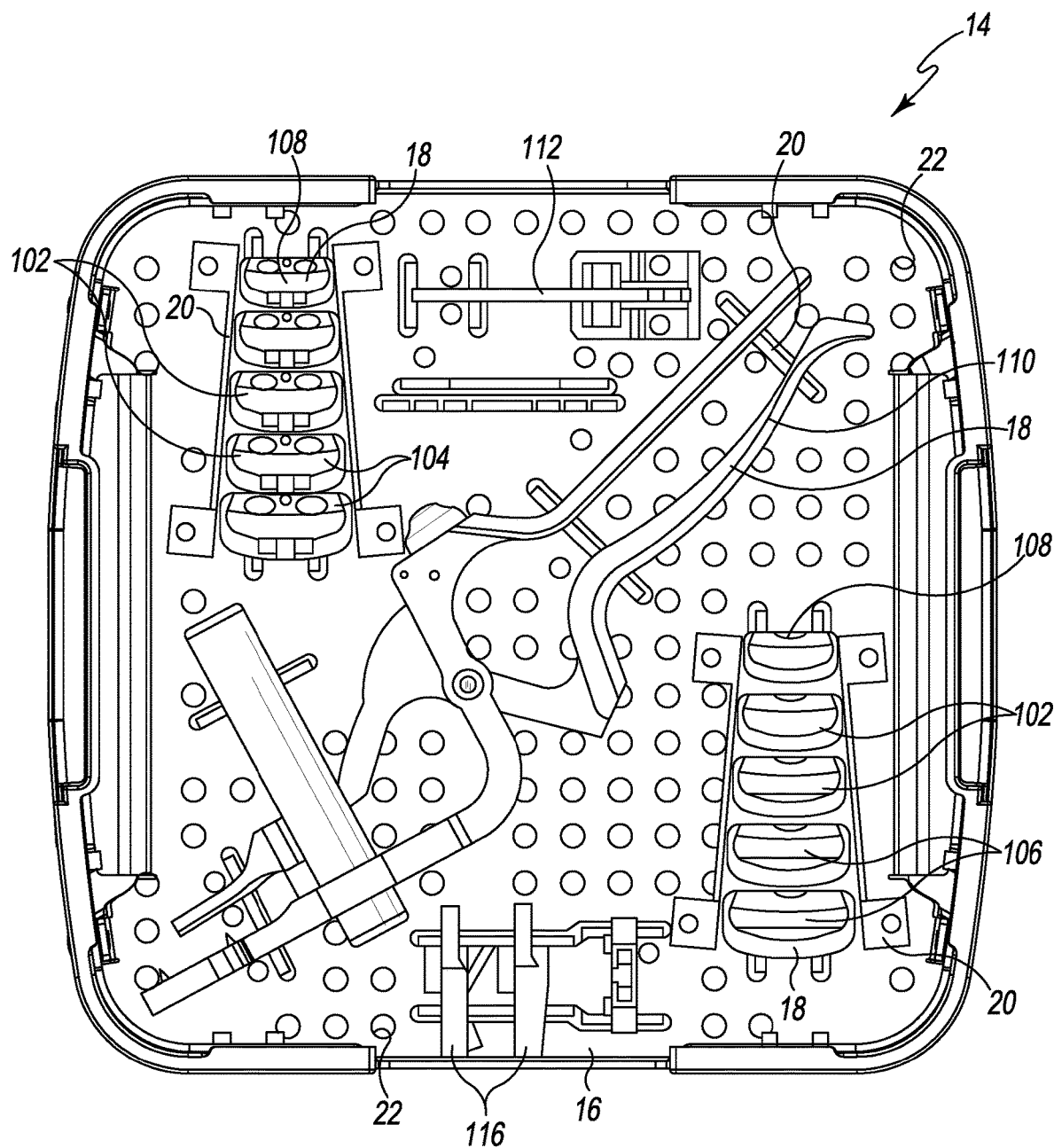
FIG. 3 is an elevation view of an exemplary embodiment of an orthopaedic surgical instrument assembly that includes patella trial components of varying types and sizes, a number of which are configured to articulate with femoral trial components of the assembly of FIG. 1.

Referring now to FIGS. 1-3, a trio of orthopaedic surgical instrument assemblies 10, 12, 14 is shown. Each of the surgical instrument assemblies 10, 12, 14 includes a sterilization tray 16 with a number of orthopaedic surgical instruments 18 positioned therein. What is meant herein by the term "orthopaedic surgical instrument" or "orthopaedic surgical instrument assembly" is a surgical tool for use by a surgeon in performing an orthopaedic surgical procedure. As such, it should be appreciated that, as used herein, the terms "orthopaedic surgical instrument" and "orthopaedic surgical instrument assembly" are distinct from orthopaedic implants or prostheses that are surgically implanted in the body of the patient.

In the exemplary embodiment described herein, a number of the orthopaedic surgical instruments 18 of the instrument assemblies 10, 12, 14 are size-specific to correspond to similarly-sized orthopaedic implants or prostheses. For example, if a product line of femoral implants is provided in sizes 1-10, femoral trial components would also be provided in sizes 1-10. In addition to trial components, femoral cutting blocks, notch guides, and finishing guides are also provided in sizes 1-10 to correspond to the size of the femoral implant being installed on the patient's femur. Similarly, if the tibial tray implants of a given product line are provided in sizes 1-10, tibial tray trial components would also be provided in sizes 1-10. If patella implants are provided in a range of sizes (e.g., 29, 32, 35, 38, 41), patella trial components would also be provided in a range of similar sizes. As such, what is meant herein by the term "size-specific" in regard to an orthopaedic surgical instrument such as a trial component or cutting block is an orthopaedic surgical instrument that is designed specifically to correspond in size with an orthopaedic implant or prosthesis of the same size. For example, a size-specific femoral trial component (e.g., size 8) is designed specifically for use during implantation of the same size femoral implant (e.g., size 8) on a patient's femur. Similarly, a size-specific tibial bearing trial component (e.g., size 6) is designed specifically for use during implantation of the same size tibial bearing implant (e.g., size 6) on a patient's tibia. It should be appreciated that many orthopaedic surgical instruments, such as saw blades, pin drivers, handles, are not size-specific. Such non-size-specific instruments are designed to be used during implantation of differently sized implants. For example, a pin driver or a system handle may be used to implant femoral components or tibial trays of any size. As such, what is meant herein by the term "non-size-specific" in regard to an orthopaedic surgical instrument is an instrument that is designed for use during implantation of differently sized implants.

The instrument sterilization trays 16 have a number of instrument retainers 20. The instrument retainers 20 are configured to retain the various differently-shaped orthopaedic surgical instruments 18 during sterilization, transport, and storage of the surgical instrument assemblies 10, 12, 14. The instrument retainers 20 may be configured as brackets, connectors, cradles, or any other type of mechanism to retain the orthopaedic surgical instruments 18 in a desired location and orientation. It should be appreciated that the instrument retainers 20 could also take the form of specifically-shaped recesses or cavities formed in the instrument sterilization tray 16 into which the orthopaedic surgical instruments 18 could be inserted and retained. As can be seen in FIGS. 1-3, some of the walls of the instrument sterilization tray 16 and some of the instrument retainers 20 have fluid holes 22 formed therein. The fluid holes 22 allow for the passage of sterilization fluid within the instrument sterilization tray 16 during the sterilization process.

The surgical instrument assembly 10 is size-specifically kitted, whereas the other two surgical instrument assemblies 12, 14 are not. In particular, the surgical instrument assembly 10 includes various types of size-specific orthopaedic surgical instruments all of which are of a common size, but no size-specific orthopaedic surgical instruments that are of a different size. What is meant herein by the terms "common size" or "commonly-sized" as they relate to two or more instruments is that the two or more instruments are all the same size. For example, a size 8 femoral trial component and a size 8 tibial bearing trial component are of a common size. However, a size 6 femoral trial component is not of a common size with a size 8 tibial bearing trial component.

In the case of the surgical instrument assembly 10, its sterilization tray 16 is kitted such that all of the size-specific orthopaedic surgical instruments 18 positioned therein are of a common size. In particular, the surgical instrument assembly 10 includes a pair of femoral trial components 30, both of which have a common size. In the illustrative embodiment of FIG. 1, the femoral trial components 30 are left and right femoral trial components, both of which are size 8. The surgical instrument assembly 10 also includes a number of tibial bearing trial components 32, all of which have a common size that is the same as the common size of the femoral trial components 30. In the illustrative embodiment of FIG. 1, the tibial bearing trial components 32 include fixed bearing trial components 36, along with rotating platform bearing trial components 38, all four of which are size 8. In the exemplary embodiment described herein, the tibial bearing trial components 32 are embodied as two-piece components having an articulation surface 42 and a tibial shim trial component 44 of a desired thickness. However, it should be appreciated that the tibial bearing trial components 32 could be embodied as a single-piece component.

In addition to trial components, in the illustrative embodiment of FIG. 1, the surgical instrument assembly 10 also includes a number of size-specific cutting instruments, all of which are the same size as the common size of the femoral trial components 30 and the tibial bearing trial components 32 (e.g., size 8). For example, the surgical instrument assembly 10 is illustratively kitted with a 4-in-1 femoral cutting block 46, a femoral notch guide 48, and a femoral finishing guide 50, all of which are the same size as the common size of the femoral trial components 30 and the tibial bearing trial components 32 (e.g., size 8).

In the illustrative embodiment of FIG. 1, the surgical instrument assembly 10 also includes a number of non-size-specific instruments. For example, a pin driver 52 is kitted along with the size-specific instruments.

Oppositely to the surgical instrument assembly 10 of FIG. 1, the surgical instrument assemblies 12, 14 include various different sizes of size-specific orthopaedic surgical instruments 18. Specifically referring to the surgical instrument assembly 12, it includes a plurality of tibial tray trial components 60, each of which is provided in a different size. For example, the tibial tray trial components 60 may be provided in six different sizes—size 3, size 4, size 5, size 6, size 7, and size 8. In the exemplary embodiment described herein, the tibial tray trial components 60 are embodied as two-piece components having a tibial plate 62 and a transfer button 64. However, it should be appreciated that the tibial tray trial components 60 could be embodied as a single-piece component. Each of the tibial tray trial components 60 includes a locking mechanism 66 that mates with a locking mechanism 68 of the tibial bearing trial components 32 such that each of the tibial bearing trial components 32 is configured to be separately coupled to each of the differently-sized tibial tray trial components 60. In the illustrative embodiment described herein, the locking mechanism 66 of the tibial tray trial components 60 is embodied as a post 70 formed on the transfer button 64, whereas the locking mechanism 68 of the tibial bearing trial components 32 is embodied as groove 72 formed in the posterior side thereof that is configured in the specific shape and size to receive the specific shape and size of the post 70 of the tibial tray trial components 60. The post 70 of each tibial tray trial components 60 is the same shape and size across the range of sizes of the tibial tray trial components 60. Similarly, the groove 72 of each tibial bearing trial components 32 is the same shape and size across the range of sizes of the tibial bearing trial components 32. In such a way, each of the tibial bearing trial components 32 may be separately coupled to each of the tibial tray trial components 60 irrespective of the specific size of either component. In the case of the illustrative embodiment described herein, each of the size 8 tibial bearing trial components 32 of the surgical instrument assembly 10 of FIG. 1 may be separately coupled to each of the tibial tray trial components 60 of the surgical instrument assembly 12 of FIG. 2 (i.e., each of the size 3, size 4, size 5, size 6, size 7, or size 8 tibial tray trial components). It should be appreciated, however, that although each of the tibial bearing insert components 32 may be physically coupled to all of the differently-sized tibial tray trial components 60, not all of such combinations may be used in practice. For example, a size 6 tibial bearing trail component may be indicated for use with a size 4, size 5, size 6, size 7, or size 8 tibial tray trial component, but not sizes smaller than size 4 or larger than size 8.

Like the surgical instrument assembly 10 of FIG. 1, in the illustrative embodiment of FIG. 2, the surgical instrument assembly 12 also includes a number of non-size-specific instruments. For example, a pin driver 80, an impactor 82, an impaction handle 84, an alignment handle 86, a tibial drill tower 88, a tibial drill 90, and a pair of tibial depth stop 92 may be kitted along with the size-specific instruments. It should also be appreciated that other non-size-specific instruments, such as tibial keel punches or the like, may also be kitted with the size-specific instruments.

Turning now to the surgical instrument assembly 14 of FIG. 3, it includes a plurality of patella trial components 102, each of which is provided in a different size. For example, the patella trial components 102 may be provided in five different sizes—size 29, size 32, size 35, size 38, and size 41. In the exemplary embodiment described herein, one set of the patella trial components 102 is embodied as a combination trial and drill guide component 104, with the other set of the patella trial components 102 being embodied as dedicated trial components 106 (i.e., they do not also function as drill guides). In the illustrative embodiment of FIG. 3, the patella trial components 102 are embodied as dome patella trial components; however, the patella trial components 102 may also be embodied as anatomic patella trial components.

The patella trial components 102 include a bearing surface 108 that is configured to articulate with the trochlear groove 54 of the femoral trial components 30. Each of the patella trial components 102 is configured to articulate with each size of the femoral trial components 30. It should be appreciated, however, that not all of such combinations may be used in practice. For example, a size 8 femoral trial component 30 may be indicated for use with a size 35, size 38, or size 41 patella trial component 102, but not size 29 or size 32 components.

In the illustrative embodiment of FIG. 3, the surgical instrument assembly 14 also includes a number of non-size-specific instruments. For example, a patella clamp 110, a patella trial handle 112, and a pair of patella button holders 116 may be kitted along with the size-specific instruments. It should also be appreciated that other non-size-specific instruments may also be kitted with the size-specific instruments.

As described above, the orthopaedic surgical instrument assembly 10 is configured as a common size system, whereas the orthopaedic surgical instrument assemblies 12, 14 are configured with varying sizes of instruments. In particular, when fully kitted and prepared for use in a surgical procedure, the orthopaedic surgical instrument assembly 10 is configured for use to implant a specific size of a femoral component on a patient's femur (along with a tibial bearing of the same size) and is, therefore, devoid of any instruments of a different size other than the size being used on the patient's femur. In other words, when the instrument sterilization tray 16 of the surgical instrument assembly 10 is fully loaded—i.e., the instrument retainers 20 have an instrument retained therein—all of the size-specific instruments retained in the retainers 20 are all of a common size. In particular, each of the size-specific instruments kitted in the orthopaedic surgical instrument assembly 10—whether it's a trial component or cutting guide—is the same size as the other size-specific components. For example, if a size 8 femoral trial component 30 is kitted in the instrument sterilization tray 16 of the surgical instrument assembly 10, then all of the tibial bearing trial components 32 and the size-specific cutting instruments (e.g., the 4-in-1 femoral cutting block 46, the femoral notch guide 48, and the femoral finishing guide 50) are all also size 8—no other sizes of size-specific instruments are included other than size 8 instruments. However, it should be appreciated that in some embodiments, non-size-specific orthopaedic surgical instruments, such as the pin driver 52, may be placed in the instrument sterilization tray 16 of the surgical instrument assembly 10 along with the commonly-sized size-specific surgical instruments.

Moreover, since the orthopaedic surgical instrument assembly 10 is configured for use to implant a specific size of a femoral component on a patient's femur (along with a tibial bearing of the same size), when it is fully kitted and prepared for use in a surgical procedure, the surgical instrument assembly 10 is devoid of any of the tibial tray trial components 60 and any of the patella trial components 102.

Oppositely, when fully kitted and prepared for use in a surgical procedure, the orthopaedic surgical instrument assemblies 12, 14 are configured with varying different sizes of size-specific instruments so that the surgeon can intraoperatively select a best-fit option to pair with the specific size of a femoral component being installed on the patient's femur (along with the tibial bearing of the same size). Specifically, when the instrument sterilization tray 16 of the surgical instrument assemblies 12, 14 are fully loaded—i.e., the instrument retainers 20 have an instrument retained therein—the size-specific instruments retained in the retainers 20 are provided in a range of varying sizes. In particular, the size-specific instruments kitted in the orthopaedic surgical instrument assembly 12—namely, the tibial tray trial components 60—are provided in a ranges of sizes. For example, the instrument sterilization tray 16 of the surgical instrument assembly 12 may be kitted with size 3, size 4, size 5, size 6, size 7, and size 8 tibial tray trial components 60. Similarly, the size-specific instruments kitted in the orthopaedic surgical instrument assembly 14—namely, the patella trial components 102—are provided in a ranges of sizes. For example, the instrument sterilization tray 16 of the surgical instrument assembly 14 may be kitted with size 29, size 32, size 35, size 38, and size 41 patella trial components 102 of one or both types (i.e., both anatomical and dome types). It should be appreciated that in some embodiments, non-size-specific orthopaedic surgical instruments, such as a pin driver, handle, or impactor, may be placed in the instrument sterilization trays 16 of the surgical instrument assemblies 12, 14 along with the size-specific surgical instruments.

Moreover, since the orthopaedic surgical instrument assemblies 12, 14 are configured for use to implant a tibial tray component or patella component, respectively, when fully kitted and prepared for use in a surgical procedure, the surgical instrument assemblies 12, 14 are devoid of any of the femoral trial components 30 or tibial bearing trial components 32.

In use, the orthopaedic surgical instrument assemblies 10, 12, 14 are used during a total knee replacement orthopaedic surgical procedure. The instrument sterilization trays 16 of the respective instrument assemblies 10, 12, 14 are first populated with the corresponding size-specific orthopaedic surgical instruments. Namely, the femoral trial components 30 and the tibial bearing components 32, all of a common size, are positioned in the instrument sterilization tray 16 of the surgical instrument assembly 10, whereas varying sizes of the tibial tray trial components 60 and varying sizes of the patella trial components 102 are positioned in the instrument sterilization trays 16 of the surgical instrument assemblies 12, 14, respectively. In such a way, the instrument sterilization tray 16 of the surgical instrument assembly 10 is devoid of any of the tibial tray trial components 60 and any of the patella components 102. Similarly, the instrument sterilization trays 16 of the surgical instrument assemblies 12, 14 are devoid of any of the femoral trial components 30 and any of the tibial bearing components 32. It should be appreciated that, in some embodiments, non-size-specific instruments may be placed in the sterilization trays 16 of any of the instrument assemblies 10, 12, 14. Once the sterilization trays 16 have been filled in such a manner, the instrument assemblies 10, 12, 14 are sterilized.

Through imaging and analysis, the surgeon preoperatively determines the size of the femoral implant to be installed on the patient's femur. Based on the size of the femoral implant to be installed on the patient's distal femur, the correspondingly sized sterilized instrument assembly 10 is then delivered to the operating room and utilized by the surgical staff during performance of the procedure. For example, if the surgeon preoperatively determines a size 8 femoral implant is to be installed on the patient's femur, a sterilized instrument assembly 10 containing size 8 instruments is selected and delivered to the operating room.

Given the instrument assemblies 12, 14 were kitted with varying sizes of the size-specific instruments, one of each of the sterilized instrument assemblies 12, 14 is selected and delivered to the operating room without regard to the preoperatively-determined size of the femoral implant to be installed on the patient's femur. For example, irrespective of whether the surgeon preoperatively-selects a size 6 or a size 7 femoral implant (or any other size), any of the sterilized instrument assemblies 12, 14 may be selected and delivered to the operating room since such assemblies 12, 14 include varying sizes of the tibial tray trial components 60 and patella trial components 102, respectively, all of which may be paired with either the size 6 or size 7 components (or any size) of the instrument assembly 10.

Kitting the instrument assemblies 10, 12, 14 in the manner described herein reduces the amount of unused instruments in the operating room since instruments for the other size of femoral implants (and associated tibial bearings) are not present. The weight of the fully-loaded trays 16 can also be reduced by not including such unneeded instruments. Moreover, by not including the unneeded instruments, post-operative cleaning and sterilization is also improved since the number of unused instruments may be reduced.

Moreover, it should be appreciated that a single configuration of the instrument assembly 10 may be used with various configurations of the instrument assemblies 12, 14. In particular, each of the instrument assemblies 12, 14 may be kitted in various different configurations such as cemented manual install, cemented robotic install, cementless manual install, and cementless robotic install. To do so, the instrument sterilization trays 16 of the instrument assemblies 12, 14 may be kitted with different types of non-size-specific instruments for use in different types of procedures to produce kits specific to such procedures. For example, one version of the instrument assemblies 12, 14 may be kitted for use in a manual cemented installation procedure with a different version of the instrument assemblies 12, 14 being kitted for use in a manual cementless installation procedure. Moreover, one version of the instrument assemblies 12, 14 may be kitted for use in a robotic cemented installation procedure with a different version of the instrument assemblies 12, 14 being kitted for use in a robotic cementless installation procedure. However, the configuration of the instrument assembly 10 remains the same irrespective of which version of the instrument assemblies 12, 14 it is being used with.

The systems and methods described herein may find particular advantages in the performance of procedures such as knee procedures. However, many of those advantages may also be recognized in instruments used in the performance of other orthopaedic knee procedures, along with procedures for other joint replacements (e.g., hip-, shoulder-, or ankle-replacement procedures).

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical instrument system, comprising:
a plurality of femoral trial components, wherein each of the plurality of femoral trial components has a single common size,
a plurality of tibial bearing trial components, wherein (i) each of the plurality of tibial bearing trial components has a size that is the same as the single common size of the plurality of femoral trial components, and (ii) each of the plurality of tibial bearing trial components includes a locking mechanism,
a plurality of tibial tray trial components, wherein (i) each of the tibial tray trial components has a size that is different from the size of at least some of the other of the plurality of tibial tray trial components, and (ii) each of the plurality of tibial tray trial components includes a locking mechanism that mates with the locking mechanisms of the plurality of tibial bearing trial components such that each of the plurality of tibial bearing trial components is configured to be separately coupled to each of the plurality of tibial tray trial components,
a first instrument sterilization tray having a plurality of instrument retainers configured to retain orthopaedic surgical instruments during sterilization and transport thereof, wherein the first instrument sterilization tray (i) has one or more of the plurality of femoral trial components and one or more of the plurality of tibial bearing trial components retained therein, with each of such retained femoral trial components and tibial bearing trial components having the single common size, and (ii) is devoid of (a) any of the plurality of tibial tray trial components, and (b) any femoral trial components or tibial bearing trial components having a size other than the single common size, and
a second instrument sterilization tray having a plurality of instrument retainers configured to retain orthopaedic surgical instruments during sterilization and transport thereof, wherein the second instrument sterilization tray (i) has the plurality of tibial tray trial components retained therein, with each of such retained tibial tray trial components having a size that is different from the size of at least some of the other retained plurality of tibial tray trial components, and (ii) is devoid of any of the plurality of femoral trial components and any of the plurality of tibial bearing trial components.

2. The surgical instrument system of claim 1, wherein the plurality of femoral trial components comprises a right femoral trial component and a left femoral trial component.

3. The surgical instrument system of claim 1, wherein the plurality of tibial bearing trial components comprises a rotating-platform tibial bearing trial component.

4. The surgical instrument system of claim 1, wherein the plurality of tibial bearing trial components comprises a fixed-bearing tibial bearing trial component.

5. The surgical instrument system of claim 1, further comprising a femoral cutting block, wherein:

the femoral cutting block has a size that is the same as the single common size of the plurality of femoral trial components, and
the first instrument sterilization tray is devoid of any of the plurality of tibial tray trial components when any of the plurality of instrument retainers of the first instrument sterilization tray has the femoral cutting block retained thereto.

6. The surgical instrument system of claim 1, further comprising a femoral notch guide, wherein:
the femoral notch guide has a size that is the same as the single common size of the plurality of femoral trial components, and
the first instrument sterilization tray is devoid of any of the plurality of tibial tray trial components when any of the plurality of instrument retainers of the first instrument sterilization tray has the femoral notch guide retained thereto.

7. The surgical instrument system of claim 1, further comprising a femoral finishing guide, wherein:
the femoral finishing guide has a size that is the same as the single common size of the plurality of femoral trial components, and
the first instrument sterilization tray is devoid of any of the plurality of tibial tray trial components when any of the plurality of instrument retainers of the first instrument sterilization tray has the femoral finishing guide retained thereto.

8. The surgical instrument system of claim 1, wherein each of the plurality of tibial tray trial components comprises a tibial plate trial component and a removable tibial post trial component.

9. The surgical instrument system of claim 1, further comprising:
a plurality of patella trial components, wherein (i) each of the patella trial components has a size that is different from the size of at least some of the other of the plurality of patella trial components, and (ii) at least one of the plurality of patella trial components includes a bearing surface configured to articulate with each of the plurality of femoral trial components, and
a third instrument sterilization tray having a plurality of instrument retainers configured to retain orthopaedic surgical instruments during sterilization and transport thereof, wherein the third instrument sterilization tray is devoid of any of the plurality of femoral trial components and any of the plurality of tibial bearing trial components when any of the plurality of instrument retainers of the third instrument sterilization tray have one of the plurality of patella trial components retained thereto.

10. A surgical instrument system, comprising:
a right femoral trial component and a left femoral component, wherein the right and left femoral trial components are the same size,
a plurality of tibial bearing trial components, wherein each of the plurality of tibial bearing trial components (i) is the same size as the right and left femoral trial components, and (ii) includes a locking mechanism,
a plurality of tibial tray trial components, wherein (i) each of the tibial tray trial components has a size that is different from the size of at least some of the other of the plurality of tibial tray trial components, and (ii) each of the plurality of tibial tray trial components includes a locking mechanism that mates with the locking mechanisms of each of the plurality of tibial bearing trial components such that each of the plurality of tibial bearing trial components is configured to be separately coupled to each of the plurality of tibial tray trial components,
a first instrument sterilization tray having a plurality of instrument retainers configured to retain orthopaedic surgical instruments during sterilization and transport thereof, wherein the first instrument sterilization tray (i) has at least one of the right and left femoral trial components, and at least one of the plurality of tibial bearing trial components retained therein, with each of such retained femoral trial components and tibial bearing trial components having a single common size, and (ii) is devoid of (a) any of the plurality of tibial tray trial components, and (b) any femoral trial components or tibial bearing trial components having a size other than the single common size, and
a second instrument sterilization tray having a plurality of instrument retainers configured to retain orthopaedic surgical instruments during sterilization and transport thereof, wherein the second instrument sterilization tray (i) has the plurality of tibial tray trial components retained therein, with each of such retained tibial tray trial components having a size that is different from the size of at least some of the other retained plurality of tibial tray trial components, and (ii) is devoid of both the right and left femoral trial components and any of the plurality of tibial bearing trial components.

11. The surgical instrument system of claim 10, wherein the plurality of tibial bearing trial components comprises a rotating-platform tibial bearing trial component.

12. The surgical instrument system of claim 10, wherein the plurality of tibial bearing trial components comprises a fixed-bearing tibial bearing trial component.

13. The surgical instrument system of claim 10, further comprising a femoral cutting block, wherein:
the femoral cutting block is the same size as the right and left femoral trial components, and
the first instrument sterilization tray is devoid of any of the plurality of tibial tray trial components when any of the plurality of instrument retainers of the first instrument sterilization tray has the femoral cutting block retained thereto.

14. The surgical instrument system of claim 10, further comprising a femoral notch guide, wherein:
the femoral notch guide is the same size as the right and left femoral trial components, and
the first instrument sterilization tray is devoid of any of the plurality of tibial tray trial components when any of the plurality of instrument retainers of the first instrument sterilization tray has the femoral notch guide retained thereto.

15. The surgical instrument system of claim 10, further comprising a femoral finishing guide, wherein:
the femoral finishing guide is the same size as the right and left femoral trial components, and
the first instrument sterilization tray is devoid of any of the plurality of tibial tray trial components when any of the plurality of instrument retainers of the first instrument sterilization tray has the femoral finishing guide retained thereto.

16. The surgical instrument system of claim 10, wherein each of the plurality of tibial tray trial components comprises a tibial plate trial component and a removable tibial post trial component.

17. The surgical instrument system of claim 10, further comprising:

a plurality of patella trial components, wherein (i) each of the patella trial components has a size that is different from the size of at least some of the other of the plurality of patella trial components, and (ii) at least one of the plurality of patella trial components includes a bearing surface configured to articulate with both the right and left femoral trial components, and a third instrument sterilization tray having a plurality of instrument retainers configured to retain orthopaedic surgical instruments during sterilization and transport thereof, wherein the third instrument sterilization tray is devoid of both the right and left femoral trial components and any of the plurality of tibial bearing trial components when any of the plurality of instrument retainers of the third instrument sterilization tray have at least one of the plurality of patella trial components retained thereto.

* * * * *